(12) United States Patent
Stout et al.

(10) Patent No.: US 6,319,224 B1
(45) Date of Patent: Nov. 20, 2001

(54) INTRADERMAL INJECTION SYSTEM FOR INJECTING DNA-BASED INJECTABLES INTO HUMANS

(75) Inventors: Richard R. Stout, West Linn; Robert A. Miller; James M. Bonicatto, both of Portland, all of OR (US)

(73) Assignee: Bioject Medical Technologies Inc., Portland, OR (US)

( * ) Notice: Subject to any disclaimer, the term of this patent is extended or adjusted under 35 U.S.C. 154(b) by 0 days.

(21) Appl. No.: 09/378,294

(22) Filed: Aug. 20, 1999

(51) Int. Cl.⁷ .................................................. A61M 5/30
(52) U.S. Cl. ........................... 604/68; 604/70; 604/140; 604/187
(58) Field of Search .................. 604/68–72, 140–143, 604/187, 131

(56) References Cited

U.S. PATENT DOCUMENTS

| | | | |
|---|---|---|---|
| 5,224,940 | * | 7/1993 | Dann et al. . |
| 5,496,290 | * | 3/1996 | Ackerman . |
| 5,520,639 | * | 5/1996 | Peterson . |
| 5,899,880 | * | 5/1999 | Bellhouse . |
| 5,957,886 | * | 9/1999 | Weston ................................... 604/68 |
| 5,993,412 | * | 11/1999 | Deily et al. ............................ 604/68 |

OTHER PUBLICATIONS

Med–e–jet inoculator brochure.

\* cited by examiner

*Primary Examiner*—Sharon Kennedy
*Assistant Examiner*—Catherine Serke
(74) *Attorney, Agent, or Firm*—Kolisch, Hartwell, Dickinson, McCormack & Heuser

(57) ABSTRACT

A system for injecting DNA-based medications into humans is provided by the present invention. The system includes a needle-free injector with an injection orifice of approximately 0.004 inches for supplying DNA-based medication at an initial pressure of from 3900 to 4300 psi, and then immediately declining to a level of about 2800 to 3800 psi, and then immediately cutting off pressure to terminate the injection. The injector includes an annular adapter for spacing the injection orifice from the skin of the patient. The adapter includes an abutment against which the injector is disposed so that the orifice is spaced approximately 0.76–1.0 inch from the skin of the patient, the adapter having an inner diameter at the distal end of approximately 0.50–0.70 inches.

20 Claims, 5 Drawing Sheets

FIG. 8 TYPICAL PRESSURE PROFILE OF A SPRING POWERED NEEDLE-FREE INJECTION DEVICE.

FIG. 9 TYPICAL PRESSURE PROFILE OF A SPRING POWERED NEEDLE-FREE INJECTION SYSTEM (FIRST 20 MILLISECONDS).

FIG. 10

TYPICAL PRESSURE PROFILE OF AN ID D.N.A. BASED INJECTION USING PREFERRED EMBODIMENT OF THE PRESENT INVENTION.

INTRADERMAL INJECTION SYSTEM FOR INJECTING DNA-BASED INJECTABLES INTO HUMANS

BACKGROUND OF THE INVENTION

Systems for delivering injections into humans have been in use for many years. The most commonly used system is a hypodermic needle attached to an ampule. To perform an injection, the needle is inserted into the tissue to the desired depth and the operator simply depresses a plunger inside the ampule to deliver the injectate. Another method less commonly used is a needle-free injection system. These systems typically consist of a device and an ampule. The device generates the power and the ampule contains the injectate. The ampule typically has a circular opening at its distal end approximately $\frac{1}{100}^{th}$ the size of its inside diameter. The device pushes the fluid out of this opening at speeds fast enough to penetrate the tissue and deposit the injectate. To perform this injection, the operator usually places the tip of the ampule against the skin of the patient and activates a trigger. For a needle-free injection system, the control of the depth of the injectate is done by the device, not the operator.

Parenteral (a route other than through the gastrointestinal tract) injections are classified according to five well established regions in which the injectate may be deposited. These are: intradermal (ID), subcutaneous (SC), intramuscular (IM), intravenous (IV)/Intraarterial (IA) and intramedullary (IMED). ID injections place the injectate in the skin or the intradermal space. SC injections place the injectate in the adipose (fat) tissue. IM injections place the injectate in the muscle. IV/IA injections place the injectate into a vein or artery. Lastly, IMED injections place the injectate in the bone marrow, spinal chord or in the medulla oblongata. Conventional needle and ampule systems can give injections in all five of these regions. Typically, needle-free injection systems are employed only for ID, SC and IM injections. The present invention relates to ID injections.

Figure 1:
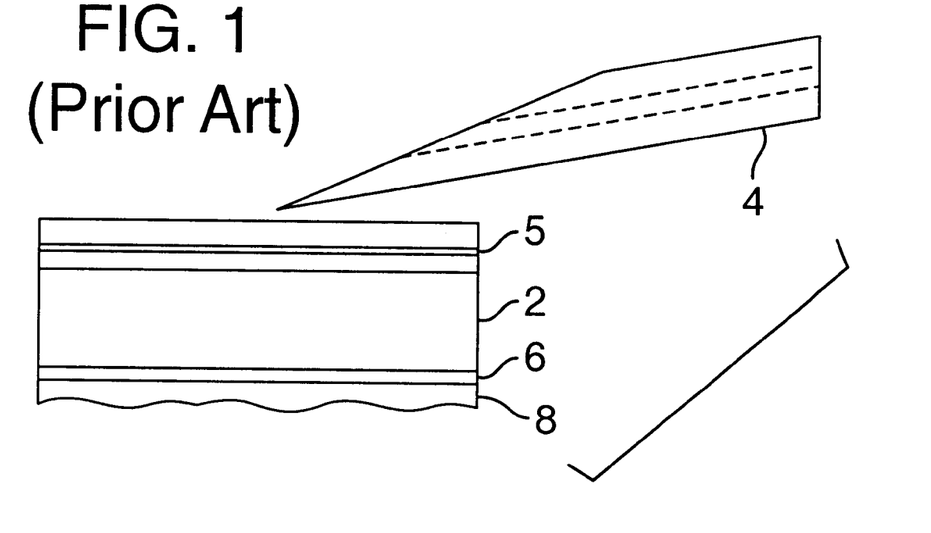
FIG. 1 is a schematic sectional view of an ID DNA-based injection using a prior art needle and ampule injection system, immediately prior to insertion of the needle into the intradermal layer of a human.
Figure 2:
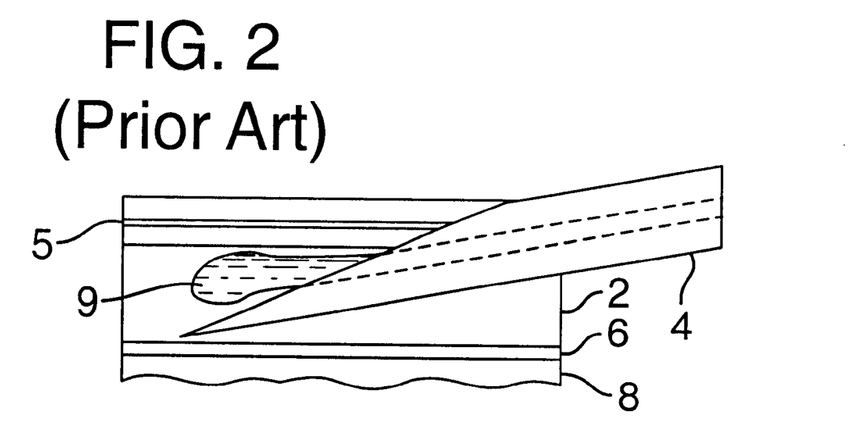
FIG. 2 is a schematic sectional view of an ID DNA-based injection corresponding to FIG. 1 except that the needle has been inserted into the intradermal layer and injectate is being injected.

A needle and ampule system can be effective for many types of ID injectables (e.g. lidocaine) because when the correct technique is employed, it can inject a predetermined amount of fluid (typical volumes range from 0.1 to 0.3 cc). A proper ID injection will appear as a raised bump on the skin surface and appear whitish in color. This bump is usually referred to as a wheal. Administering a proper ID injection using a conventional needle and ampule injection system can be difficult. The space in which the tip of the needle must be placed is very small (about 1 mm). This space is usually referred to as the intradermal space, and is indicated schematically in FIGS. 1 and 2 at 2. The shaft of the needle 4 must be held at a very shallow angle with respect to the target surface, usually 5° to 15°, and be held in a particular orientation. It is critical that the needle tip pass most of the way through the outer layer of skin, typically called the epidermis 5, but that the tip not penetrate the superficial fascia 6 (the tissue layer that separates the skin layer from the underlying adipose layer 8), or the volume of injectate 9 will not be delivered entirely in the intradermal space 2. Thus, an ID injection with a needle and ampule system requires an exacting technique from the user to give a proper injection. The clinician can determine whether a proper ID injection has been administered by lightly pressing on the wheal; if it disappears or flattens out, then the injection was not truly intradermal. If the needle penetrates the superficial fascia, the injectate will enter the adipose layer. This happens frequently with conventional ID injections and the only solution is to repeat the procedure until a satisfactory injection is given. This can be uncomfortable for the patient and frustrating for the clinician.

In the last few years, a substantial effort has been directed into the development of new types of vaccines and therapies. The term "Deoxyribonucleic Acid (DNA)-based injectables" refers to this new type of injectables. DNA is defined as a carrier of genetic information. Vaccines are defined as any preparation intended for active immunological prophylaxis (prevention of a disease). Therapies are defined as the treatment of a disease or disorder by various methods. DNA-based injectables promises to be an exciting new tool for the prevention and treatment of disease.

Briefly, the overall goal of an ID DNA-based injection is to prevent or treat disease. On a cellular level, the goal is to achieve transfection and expression. Transfection is defined as a method of gene transfer utilizing infection of a cell with nucleic acid (as from a retrovirus) resulting in subsequent viral replication in the transfected cell. Expression is defined as the cell's ability to produce the antigen. An antigen is any substance that, as a result of coming into contact with appropriate cells, induces a state of sensitivity and/or immune responsiveness after a latent period (days to weeks) and which reacts in a demonstrable way with antibodies and/or immune cells of the sensitized subject in vivo or in vitro. Transfection of DNA-based medications is enhanced by utilizing injection techniques that deposit the injectate over a large area at a sufficient pressure to ensure transfection, and cause a certain amount of local tissue disruption, encouraging an immune response. It is an object of the present invention to develop a needle-free injection system which is particularly suitable for ID DNA-based injectables.

SUMMARY OF THE INVENTION

A system for injecting DNA-based intradermal medications into humans is provided by the present invention. The system includes a needle-free injector with an injection orifice of approximately 0.004 inches for supplying DNA-based medication at an initial pressure of from 3900 to 4300 psi, and then immediately declining to a level of about 2800 to 3800 psi, and then immediately cutting off pressure to terminate the injection. The injector includes an annular adapter for spacing the injection orifice from the skin of the patient. The adapter includes an abutment against which the injector is disposed so that the orifice is spaced approximately 0.76–1.0 inch from the skin of the patient, the adapter having an inner diameter at the distal end of approximately 0.50–0.70 inches.

DETAILED DESCRIPTION OF THE PREFERRED EMBODIMENT

The needle-free injection system described herein can effectively administer ID injectables with the same volume range of injectables as the needle and ampule system without any significant user skill or training. To increase the efficiency of ID injections, an ID adapter was developed that attaches to the distal end of the ampule of the preferred embodiment of the present invention: the needle-free injection system described in U.S. Pat. No. 5,399,163 or that described in pending U.S. application Ser. No. 08/858,249, both of which are incorporated herein by reference. For either system, the actual injection site on the body can be in many different locations (e.g. the medial side of the forearm or around the knee).

In the preferred embodiment of the present invention, an intradermal adapter, shown at 12, is coupled to the needle-free injection system described in U.S. Pat. No. 5,399,163 or that described in pending U.S. application Ser. No. 08/858,249, the ampule portion of which is indicated generally and schematically at 10. Intradermal adapter 12 is annular in cross section. It spaces the tip of an ampule 14 off the skin approximately 0.76–1.0 inches, and preferably about 0.79 inches, and has an inside diameter of approximately 0.50–0.70 inches, preferably about 0.60. This system increases the efficiency of an ID DNA-based injection when compared to conventional needle and ampule systems, as well as other available needle-free injection systems.

The preferred embodiment of the present invention also envisions a method of injecting a predetermined amount of DNA-based injectate at an ID site. Using the needle-free injection system of the preferred embodiment ensures that the DNA-based injectate is suitably spread throughout the intradermal space to maximize the likelihood that the injectate will cause the desired immunological response. The goal of the preferred embodiment of the present invention is to deliver DNA-based injectables to an ID site so that the body's immune system is systemically activated to a degree not previously achieved with needle and ampule and other needle-free injection systems.

One method to increase the effectiveness of an ID DNA-based injection is to increase the speed at which the genetic message is delivered to the immune system. This can be accomplished in many ways. Two such methods are: 1) to increase the quantity of cells transfected by depositing all of the injectate over as large an area as possible in the target site at a sufficient pressure to ensure transfection; and 2) to administer an ID injection that causes a certain amount of local tissue disruption to occur, which will encourage an immune response. The preferred embodiment of the present invention does increase the speed at which the genetic message is delivered to the immune system. It does so by the two means suggested above.

Figure 3:
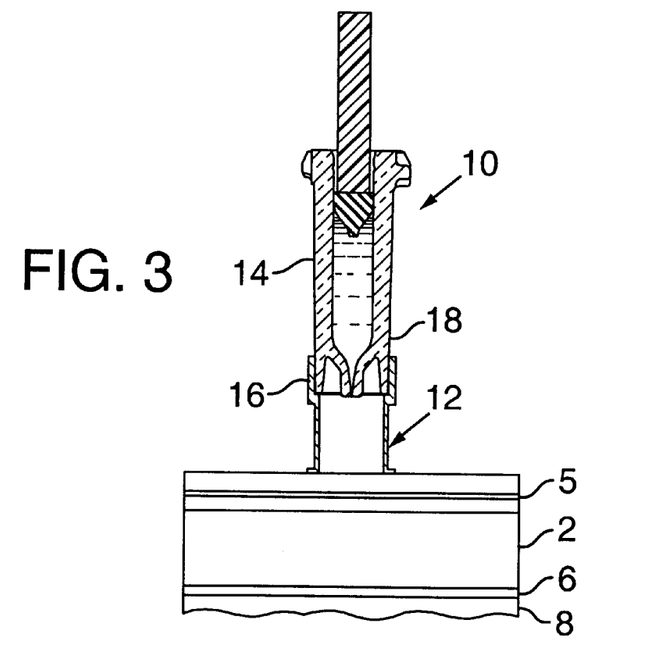
FIG. 3 is a schematic side elevation sectional view of the preferred embodiment, with the adapter in place and the device resting against the skin of the patient.
Figure 4:
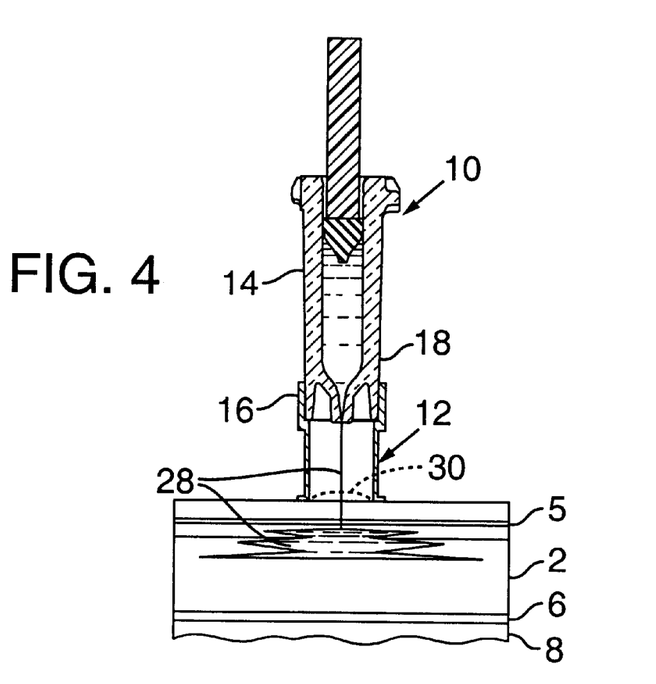
FIG. 4 is a schematic side elevation sectional view corresponding to FIG. 3 except that the injection is in the process of taking place.
Figure 5:
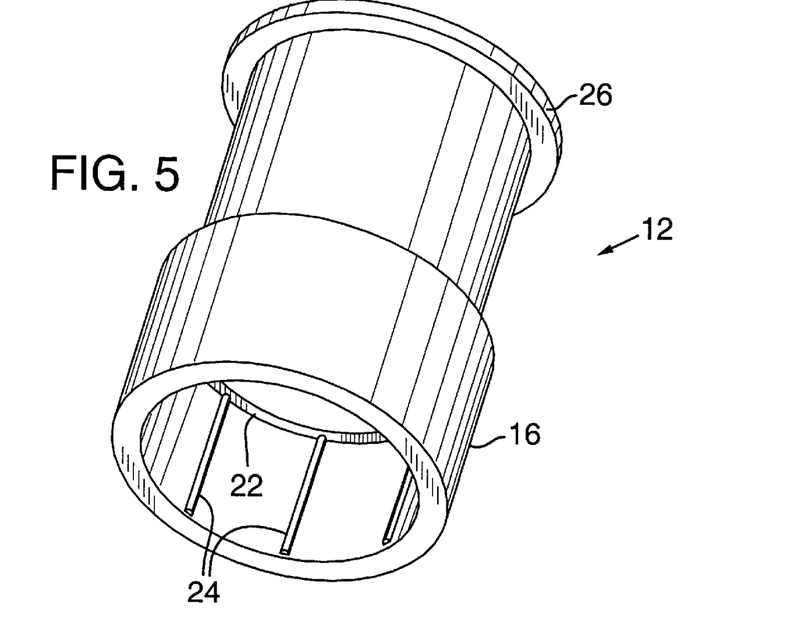
FIG. 5 is an isometric view of the intradermal adapter of the preferred embodiment.

FIGS. 3 and 4 show a schematic cross-section of an ID injection using the preferred embodiment of the present invention with a DNA-based injectable being directed through the many layers of skin tissue. The dispersion pattern deposits the injectate over a large area under sufficient pressure to increase transfection. It is quite different from the pooling or bolus which results from a conventional ampule and needle injection (see FIG. 2). Second, local tissue disruption is caused in the layers of the skin again by the dispersion pattern. This local tissue disruption is different than the cell transfection described earlier in that transfection occurs at the cellular level and in this context, tissue disruption occurs as separation of the many layers of skin without penetration through the superficial fascia (see FIG. 4). Thus, an immune response is activated due to the local tissue disruption.

Figure 6:
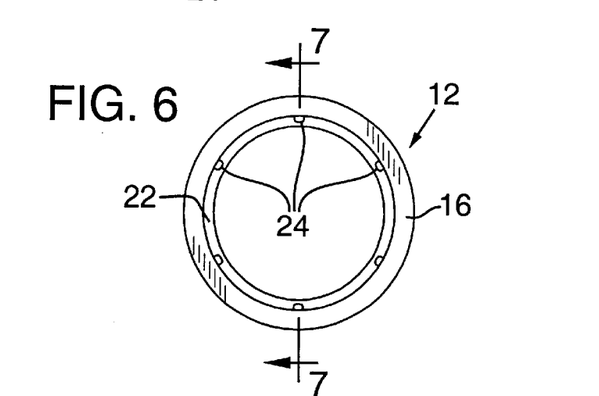
FIG. 6 is an end elevation view of the intradermal adapter of FIGS. 3–5.
Figure 7:
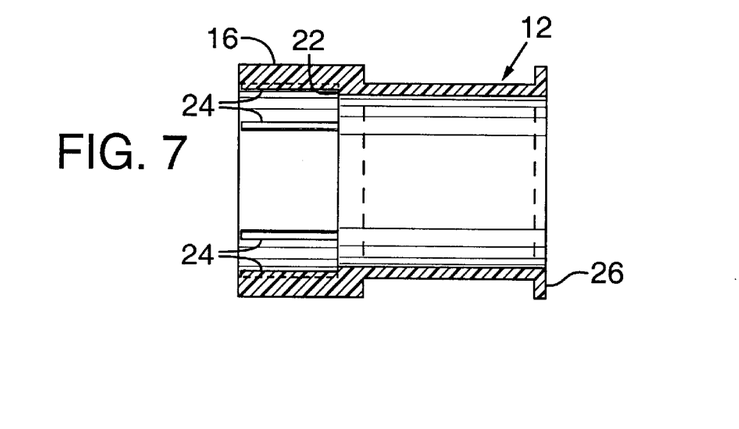
FIG. 7 is a side elevation sectional view taken along line 7—7 of FIG. 6.

The proper distribution of injectate through the intradermal space is dependent upon three variables: 1) the ampule tip should be at the proper distance from the skin (i.e. 0.76 to 1.0 inches); 2) the diameter of the adapter where skin contact is made should be within certain parameters (i.e. 0.50 to 0.70 inches); and 3) the injectate must be delivered at the proper pressure and for the appropriate period of time. As depicted in FIGS. 3 and 4, the proximal end 16 of adapter 12 is slipped over the distal end 18 of ampule 14. The proximal end 16 of adaptor 12 is enlarged, creating a shoulder or abutment 22 (see FIGS. 6–7). Axial ribs 24 cooperate with abutment 22 to ensure that the adapter is properly positioned on ampule 14. Adapter 12 also has an enlarged flange or contact ring 26 at its distal end for stability. The outer diameter of contact ring 26 is normally between 0.70 and 0.90 inches, or at least about 0.20 inches greater than the inner diameter of adapter 12.

The reason it is important to space the tip of the ampule off the skin by the given amount is to ensure penetration to the proper depth. Proper adapter sizing is important to ensure that the device does not interfere with the formation of the ID wheal. The lower limit of its size was determined by noting the wheal diameter that was formed for the largest expected volume. The upper limit was determined by physical constraints such as injection site.

With the preferred embodiment, injectate 28 is directed out of the orifice of ampule 14, through the epidermis 5 and into the intradermal space 2. The wheal (shown in phantom at 30) will typically form above the injection site. The wheal is depicted in phantom because it does not typically form until immediately after the injection.

Figure 10:
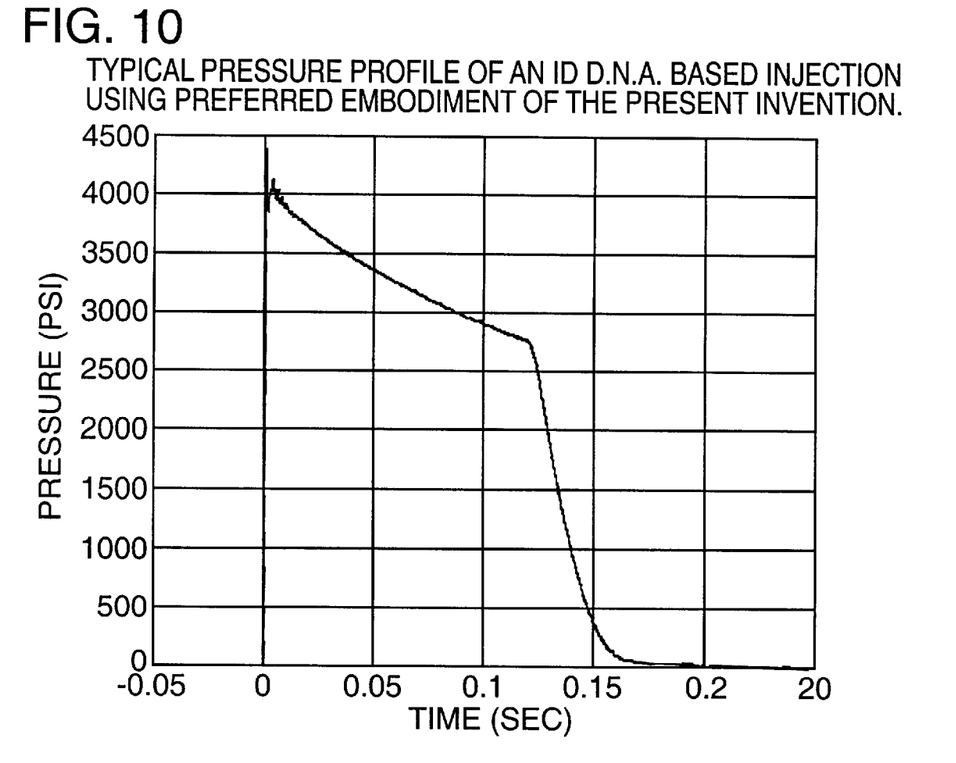
FIG. 10 is a typical pressure profile of the preferred embodiment of the present invention.

As depicted in FIG. 10, the pressure of the injectate inside the ampule should rapidly rise to a peak pressure of 3900–4300 psi, preferably to about 4100 psi, in less than 5 milliseconds, and preferably in 1 millisecond or less. This phase of the injection is termed the penetration phase. In the penetration phase, the skin tissue is penetrated. The peak pressure should be in the range given to ensure penetration of the skin. Injectate pressures below this peak value are not sufficient to consistently pierce the skin layer. Injectate pressures above the range would penetrate too deep. The quick pressure rise is necessary to instantly penetrate to the desired level and avoid any injectate coming back through the tissue, a phenomenon known as "splash-back".

Next the injectate pressure inside the ampule is dropped to about 2800–3800 psi. This phase of the injection, termed the delivery phase, is when the predetermined volume of the ID DNA injectate is delivered to the intradermal space. It is in this phase that the benefits of the needle-free injection system described herein can be noted. The injectate disperses out over a relatively large area (compared with the needle and ampule injection system). This is basically due to the $CO_2$ gas power source used in the preferred embodiment of the present invention. The $CO_2$ gas, coupled with the proper pressure regulating valves and mass flow controls, provides a stable energy source throughout the injection. This translates to a large (between 1200 and 2500 psi) and steady (no significant pressure fluctuations) delivery pressure in the ampule. Another consequence of this large and steady delivery pressure is local tissue disruption which appears as separation of the many layers of skin without penetration through the superficial fascia (see FIG. 2).

Finally, at the end of the injection, a plunger inside the ampule will bottom-out on the ampule itself This is the only mechanism that stops the injection. Thus, the driving force on the plunger remains high until all the injectate is delivered and because of the plunger-ampule impact, the residual injectate pressure drops to atmospheric pressure in less than 10 milliseconds. The effect of this characteristic is to deliver the entire volume to the desired depth and to prevent the injectate from leaking back through the tissue, a phenomenon known as "leak-back".

FIG. 10 depicts a typical pressure profile for a ¼cc ID injection using the preferred embodiment of the present invention. The term "pressure profile" is defined as a graph of injectate pressure in the ampule vs. time. Data were collected with a pressure transducer mounted on the ampule so that the sensing element was exposed to the injectate (just upstream of the start of the nozzle) without interfering with the injection. The transducer had a resolution of 0.20 psi and a linearity of 2% full scale. The transducer was connected to a PC-based data acquisition system, which consisted of a personal computer, application software, data acquisition board, signal conditioning unit and a power supply. A scan rate of 10,000 samples per second was found to be fast enough to capture the event. This figure shows the injectate pressure in the ampule rising to a peak of about 4300 psi in about 1 millisecond. Immediately following the peak pressure, a 800 psi drop in pressure occurs (down to about 3500 psi) for roughly 1 millisecond. The ampule pressure then returns to its original peak pressure. This phenomenon is probably due to the compliance of the ampule. That is, the ampule was designed to be stiff to easily withstand the pressure, but since its not a perfectly rigid structure, it swells slightly under the large imposed pressure. This swelling means that the diameter of the ampule actually increases slightly, for about 1 millisecond. Apparently, some energy is being used to induce this swelling which would otherwise go into pressurizing the fluid. Simultaneously, the ampule plunger transitions from the initial impact to more of a steady state condition (analogous to the penetration and delivery phase discussed earlier), fluid is expelled out of the small orifice at the distal end of the ampule and the ampule relaxes to its nominal size. This causes the pressure to rebound to its original level. This phenomenon could account for the quick drop and rebound in pressure following the peak pressure. Subsequent pressure fluctuations are much smaller in magnitude (approximately 100 psi) and probably are caused by the same phenomenon, just on a smaller scale. Although this phenomenon was not part of the design intent, it has no measurable effect on the ID injection and is therefore considered to be tolerable. The curve starts to become truly smooth at about 20 milliseconds and continues to remain so until the end of the injection.

Figure 8:
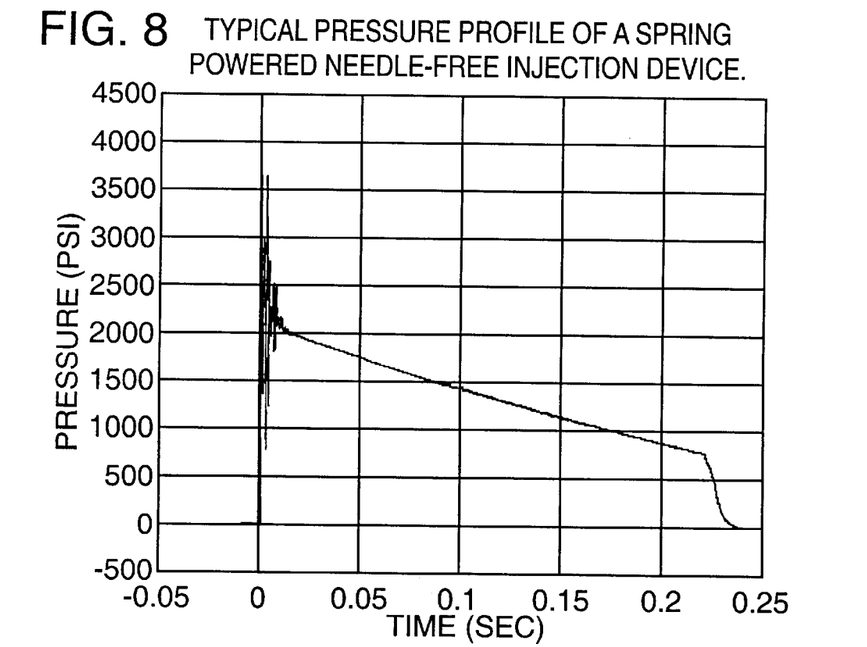
FIG. 8 is a typical pressure profile of a prior art spring powered needle-free injection system.
Figure 9:
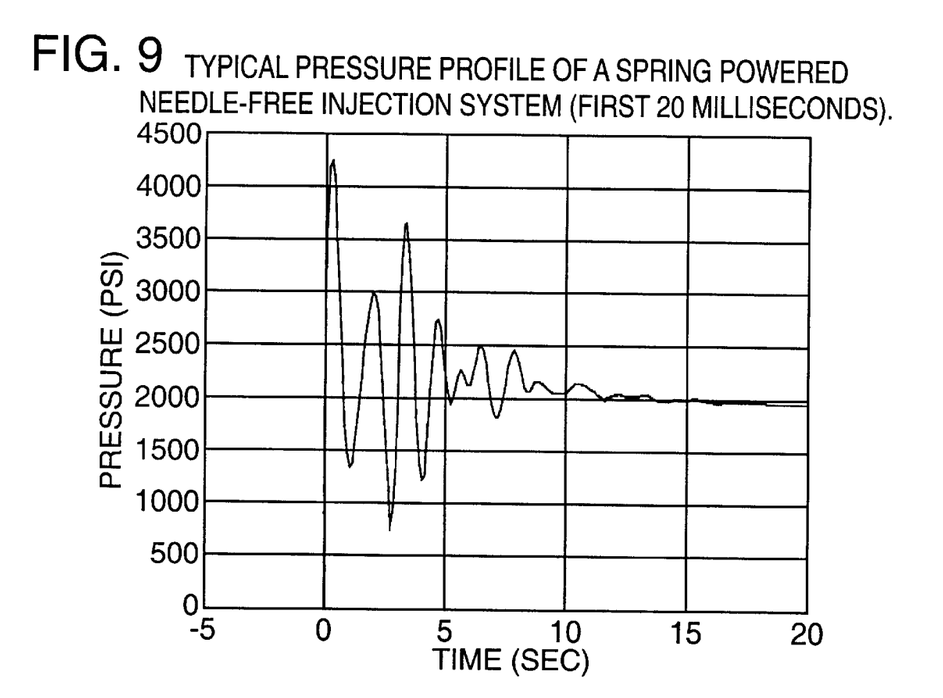
FIG. 9 is the first 20 milliseconds of a typical pressure profile of a prior art spring powered needle-free injection system.

An example of a situation where the pressure fluctuations might be significant for ID DNA-based injections can be found in needle-free injection systems that use a mechanical or gas spring as a power source. These type of devices are normally used for SC injections. Typically, these devices use a compressed spring to drive the ampule plunger and administer the injection. FIG. 8 shows a typical pressure profile for a mechanical spring powered needle-free injection system. The data were acquired with the same system mentioned previously. In these systems, as with the preferred embodiment of the present invention, the pressure in the ampule rises rapidly to its peak of about 4100 psi in less than 1 millisecond. However, for the next 9 milliseconds or so, significant pressure oscillations can be seen. At one point, a drop of about 2800 psi occurs (see FIG. 9). This pressure oscillation translates to a pulsating fluid stream which would have three effects on an attempted ID DNA injection: 1) the entire volume would not be deposited at the desired depth (i.e. the superficial fascia would be penetrated); 2) the dispersion pattern would not be optimal; and 3) tissue disruption would occur at all tissue layers, rather than just in the target layer (i.e. intradermal space). Another drawback to using a spring as a power source is that the ampule pressure at the end of the injection is typically very low (roughly 700 psi). This pressure is simply too low to ensure that all the injectate is deposited in the intradermal space.

Changes and modifications of the present invention can be made without departing from the spirit and scope of the present invention. Such changes and modifications are intended to be covered by the following claims:

What is claimed is:

1. A method for performing intradermal injection of liquid injectables into humans, comprising:

fitting, adjacent an injection orifice of a needle-free injector, the proximal end of a substantially cylindrical intradermal adapter having a proximal and distal end and an internal abutment against which the injector is disposed to provide a fixed spacing of from approximately 0.76 to 1.0 inches from the injection orifice to the distal end of the adapter, the distal end having an inner diameter of from 0.50 to 0.70 inches;

selecting the needle-free injector having the injection orifice of from 0.004 to 0.005 inches;

holding the distal end of the intradermal adapter against the skin of the patient; and using the needle-free injector to inject a liquid injectable in a volume of 0.3 ml or less into the intradermal region at an initial peak pressure of from 3900 to 4300 psi, and then permitting the injection pressure to decay to a level of about 2300 to 3800 psi, after which time the pressure is abruptly cut off, terminating the injection;

wherein, following a single quick drop and rebound in pressure following the initial peak pressure, there is no more than plus or minus 100 psi variation from the pressure curve of the injection.

2. A method of delivering liquid injectables intradermally, using a needle-free injection system, comprising the steps of:

pressurizing a liquid injectable within an ampule having a nozzle orifice to an initial peak pressure adjacent the nozzle orifice of approximately 3900–4300 psi within 5 milliseconds, while spacing the nozzle orifice off the skin by approximately 0.76 to 1.0 inches using an intradermal adapter with an internal diameter of approximately 0.5 to 0.70 inch, thus penetrating the skin tissue;

gradually and continuously reducing the pressure within the range of approximately 2300–3800 psi, during a substantial portion of which reduction the pressure decreases in a substantially linear manner, thereby distributing the entire volume of the liquid injectable over a large area in the intradermal space, causing local tissue disruption within the intradermal space, thereby encouraging an immune response; and at the end of the injection, abruptly terminating the ampule pressure within 10 milliseconds, thus ensuring that the entire volume is delivered to the desired depth and avoiding any injectate leaking back through the tissue.

3. The method of claim 2, wherein the pressure of the liquid injectable at any point after the initial peak pressure is achieved, does not change more than 1000 psi in 1 millisecond or less.

4. The method of claim 2, wherein, the pressure of the liquid injectable has no more than one drop in pressure greater than 500 psi in less than 2 milliseconds during the first 10 milliseconds of the injection.

5. The method of claim 2, wherein the peak pressure is about 3900–4300 psi, the reduced pressure ranges between about 2300–3800 psi, and the pressure cut-off occurs within about 10 milliseconds.

6. The method of claim 2, wherein the volume of liquid injectable is less than or equal to 0.3 ml.

7. The method of claim 2, wherein the intradermal adapter is generally cylindrical and the distal end of the adapter terminates in a flange extending radially outward from the adapter and wherein the outer diameter of the said flange is at least about 0.2 inches greater than the inner diameter.

8. The method of claim 2, wherein the intradermal adaptor includes an abutment that fixes the nozzle orifice at a single, specific distance of between approximately 0.76–1.0 inch from the skin of the patient.

9. The method of claim 2, wherein the liquid injectable is DNA-based.

10. A method for performing intradermal injection of liquid injectables into humans, comprising:

fitting, adjacent an injection orifice of a needle-free injector, the proximal end of a substantially cylindrical intradermal adapter having a proximal and distal end and an internal abutment against which the injector is disposed to provide a fixed spacing of from approximately 0.76 to 1.0 inches from the injection orifice to the distal end of the adapter, the distal end having an inner diameter of from 0.50 to 0.70 inches;

selecting the needle-free injector having the injection orifice of from 0.004 to 0.005 inches;

holding the distal end of the intradermal adapter against the skin of the patient; and using the needle-free injector to inject a liquid injectable in a volume of 0.3 ml or less into the intradermal region at an initial peak pressure of from 3900 to 4300 psi, and then permitting the injection pressure to decay to a level of about 2300 to 3800 psi, after which time the pressure is abruptly cut off, terminating the injection;

wherein the pressure of the liquid injectable continuously declines within the range between about 2300 and 3800 psi from the time immediately after the initial peak pressure is achieved until the injection ends abruptly.

11. The method of claim 10, wherein pressure decreases substantially linearly for a substantial portion of the pressure decline occurring after the initial peak pressure is achieved and prior to termination of the injection.

12. The method of claim 10 or claim 2, wherein pressure decreases substantially linearly for the latter half of the pressure decline occurring after the initial peak pressure is achieved and prior to termination of the injection.

13. The method of claim 10 or claim 2, wherein pressure decreases in a substantially linear manner from about 0.05 second after the initial pressure is achieved until the injection terminates abruptly.

14. A method for performing intradermal injection of liquid injectables into humans, comprising:

fitting, adjacent an injection orifice of a needle-free injector, the proximal end of a substantially cylindrical intradermal adapter having a proximal and distal end and an internal abutment against which the injector is disposed to provide a fixed spacing of from approximately 0.76 to 1.0 inches from the injection orifice to the distal end of the adapter, the distal end having an inner diameter of from 0.50 to 0.70 inches;

selecting the needle-free injector having the injection orifice of from 0.004 to 0.005 inches;

holding the distal end of the intradermal adapter against the skin of the patient; and using the needle-free injector to inject a liquid injectable in a volume of 0.3 ml or less into the intradermal region at an initial peak pressure of from 3900 to 4300 psi, and then permitting the injection pressure to decay to a level of about 2300 to 3800 psi, after which time the pressure is abruptly cut off, terminating the injection;

wherein the injector injects the liquid injectable into the intradermal space, thereby depositing the medication over as large an area as possible and causing local tissue disruption within the intradermal space, which may activate an immune response.

15. A method for performing intradermal injection of liquid injectables into humans, comprising:

fitting, adjacent an injection orifice of a needle-free injector, the proximal end of a substantially cylindrical intradermal adapter having a proximal and distal end and an internal abutment against which the injector is disposed to provide a fixed spacing of from approximately 0.76 to 1.0 inches from the injection orifice to the distal end of the adapter, the distal end having an inner diameter of from 0.50 to 0.70 inches;

selecting the needle-free injector having the injection orifice of from 0.004 to 0.005 inches;

holding the distal end of the intradermal adapter against the skin of the patient; and using the needle-free injector to inject a liquid injectable in a volume of 0.3 ml or less into the intradermal region at an initial peak pressure of from 3900 to 4300 psi, and then permitting the injection pressure to decay to a level of about 2300 to 3800 psi, after which time the pressure is abruptly cut off, terminating the injection;

wherein the pressure of the liquid injectable at any point after the initial peak pressure is achieved, does not change more than 1000 psi in 1 millisecond or less.

16. A method for performing intradermal injection of liquid injectables into humans, comprising:

fitting, adjacent an injection orifice of a needle-free injector, the proximal end of a substantially cylindrical intradermal adapter having a proximal and distal end and an internal abutment against which the injector is disposed to provide a fixed spacing of from approximately 0.76 to 1.0 inches from the injection orifice to the distal end of the adapter, the distal end having an inner diameter of from 0.50 to 0.70 inches;

selecting the needle-free injector having the injection orifice of from 0.004 to 0.005 inches;

holding the distal end of the intradermal adapter against the skin of the patient; and using the needle-free injector to inject a liquid injectable in a volume of 0.3 ml or less into the intradermal region at an initial peak pressure of from 3900 to 4300 psi, and then permitting the injection pressure to decay to a level of about 2300 to 3800 psi, after which time the pressure is abruptly cut off, terminating the injection;

wherein, the pressure of the liquid injectable has no more than one drop in pressure greater than 500 psi in less than 2 milliseconds during the first 10 milliseconds of the injection.

17. A method for performing intradermal injection of liquid injectables into humans, comprising:

fitting, adjacent an injection orifice of a needle-free injector, the proximal end of a substantially cylindrical intradermal adapter having a proximal and distal end and an internal abutment against which the injector is disposed to provide a fixed spacing of from approximately 0.76 to 1.0 inches from the injection orifice to the distal end of the adapter, the distal end having an inner diameter of from 0.50 to 0.70 inches;

selecting the needle-free injector having the injection orifice of from 0.004 to 0.005 inches;

holding the distal end of the intradermal adapter against the skin of the patient; and using the needle-free injector to inject a liquid injectable in a volume of 0.3 ml or less into the intradermal region at an initial peak pressure of from 3900 to 4300 psi, and then permitting the injection pressure to decay to a level of about 2300 to 3800 psi, after which time the pressure is abruptly cut off, terminating the injection;

wherein the peak pressure is about 3900–4300 psi, the reduced pressure ranges between about 2300–3800 psi, and the pressure cut-off occurs within about 10 milliseconds.

18. A method for performing intradermal injection of liquid injectables into humans, comprising:

fitting, adjacent an injection orifice of a needle-free injector, the proximal end of a substantially cylindrical intradermal adapter having a proximal and distal end and an internal abutment against which the injector is disposed to provide a fixed spacing of from approximately 0.76 to 1.0 inches from the injection orifice to the distal end of the adapter, the distal end having an inner diameter of from 0.50 to 0.70 inches;

selecting the needle-free injector having the injection orifice of from 0.004 to 0.005 inches;

holding the distal end of the intradermal adapter against the skin of the patient; and using the needle-free injector to inject a liquid injectable in a volume of 0.3 ml or less into the intradermal region at an initial peak pressure of from 3900 to 4300 psi, and then permitting the injection pressure to decay to a level of about 2300 to 3800 psi, after which time the pressure is abruptly cut off, terminating the injection;

wherein the volume of liquid injectable is less than or equal to 0.3 ml.

19. A method for performing intradermal injection of liquid injectables into humans, comprising:

fitting, adjacent an injection orifice of a needle-free injector, the proximal end of a substantially cylindrical intradermal adapter having a proximal and distal end and an internal abutment against which the injector is disposed to provide a fixed spacing of from approximately 0.76 to 1.0 inches from the injection orifice to the distal end of the adapter, the distal end having an inner diameter of from 0.50 to 0.70 inches;

selecting the needle-free injector having the injection orifice of from 0.004 to 0.005 inches;

holding the distal end of the intradermal adapter against the skin of the patient; and using the needle-free injector to inject a liquid injectable in a volume of 0.3 ml or less into the intradermal region at an initial peak pressure of from 3900 to 4300 psi, and then permitting the injection pressure to decay to a level of about 2300 to 3800 psi, after which time the pressure is abruptly cut off, terminating the injection;

wherein the intradermal adapter is generally cylindrical and the distal end of the adapter terminates in a flange extending radially outward from the adapter and wherein the outer diameter of the said flange is at least about 0.2 inches greater than the inner diameter.

20. A method for performing intradermal injection of liquid injectables into humans, comprising:

fitting, adjacent an injection orifice of a needle-free injector, the proximal end of a substantially cylindrical intradermal adapter having a proximal and distal end and an internal abutment against which the injector is disposed to provide a fixed spacing of from approximately 0.76 to 1.0 inches from the injection orifice to the distal end of the adapter, the distal end having an inner diameter of from 0.50 to 0.70 inches;

selecting the needle-free injector having the injection orifice of from 0.004 to 0.005 inches;

holding the distal end of the intradermal adapter against the skin of the patient; and using the needle-free injector to inject a liquid injectable in a volume of 0.3 ml or less into the intradermal region at an initial peak pressure of from 3900 to 4300 psi, and then permitting the injection pressure to decay to a level of about 2300 to 3800 psi, after which time the pressure is abruptly cut off, terminating the injection;

wherein the liquid injectable is DNA-based.

* * * * *